United States Patent [19]
Hess

[11] Patent Number: 5,611,207
[45] Date of Patent: Mar. 18, 1997

[54] CRYOGENIC INTERFACE FOR PERPENDICULAR LOADING OF INDEPENDENT MEASUREMENT INSERTS

[76] Inventor: John Hess, 518 N. Plumer Ave., Tucson, Ariz. 85719

[21] Appl. No.: 496,428

[22] Filed: Jun. 29, 1995

[51] Int. Cl.[6] .................................................. F25B 19/00
[52] U.S. Cl. ............................................. 62/51.1; 62/298
[58] Field of Search ...................................... 62/51.1, 298

[56] References Cited

U.S. PATENT DOCUMENTS

| | | | |
|---|---|---|---|
| 4,535,596 | 8/1985 | Laskaris | 62/51.1 |
| 4,635,450 | 1/1987 | Laskaris | 62/51.1 |
| 5,216,889 | 6/1993 | Herd et al. | 62/51.1 |

*Primary Examiner*—Ronald C. Capossela

[57] ABSTRACT

A cryogenically efficient interface which enables the quick loading of completely configured Independent Measurement Inserts in a direction perpendicular to the temperature gradient of a cryogenic cooling source. An air lock and pre-cooling means provide a method for loading independent measurement inserts directly into the cryostat vacuum without applying an undue initial or steady thermal load on the cooling source. A heat switch provides means for establishing variable thermal contact between the contoured independent measurement inserts and the cold stage of a cryogenic cooling source. There is a free selection in the cryogenic cooling source which may be used and also in the types of measurements which may be configured and loaded by the means of appropriately configured idependent measurement inserts. Loading of measurement inserts may be carried out in any direction. The experimental flexibility gained in the use of my invention is a benefit to scientists and engineers wishing to conveniently perform a diversity of different measurements at cryogenic temperatures.

10 Claims, 19 Drawing Sheets

FIG 7
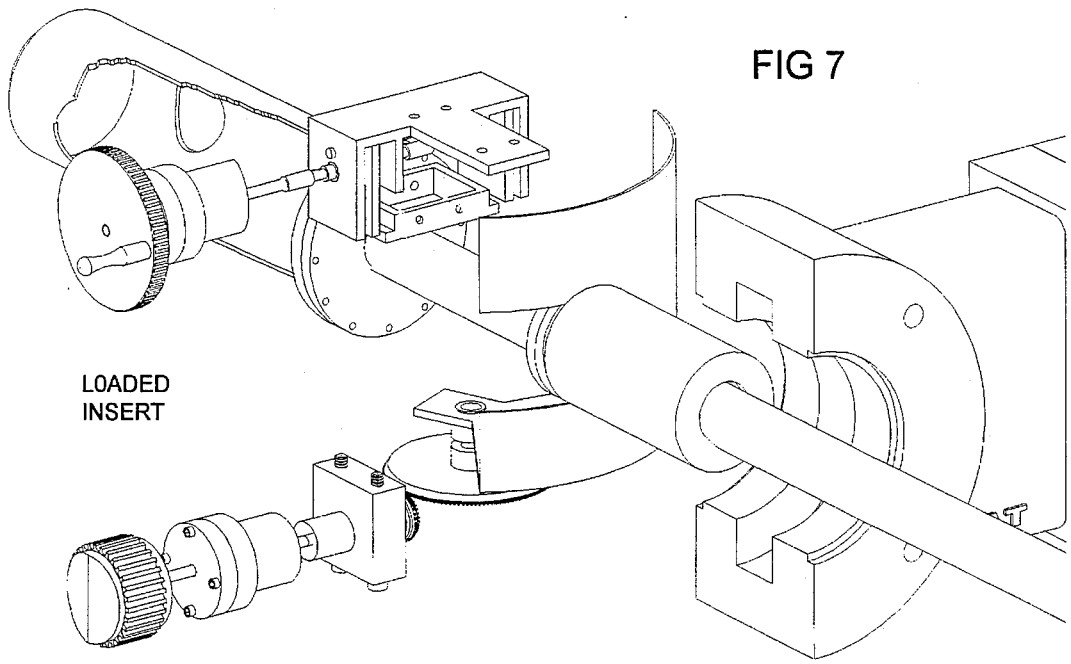
LOADED
INSERT
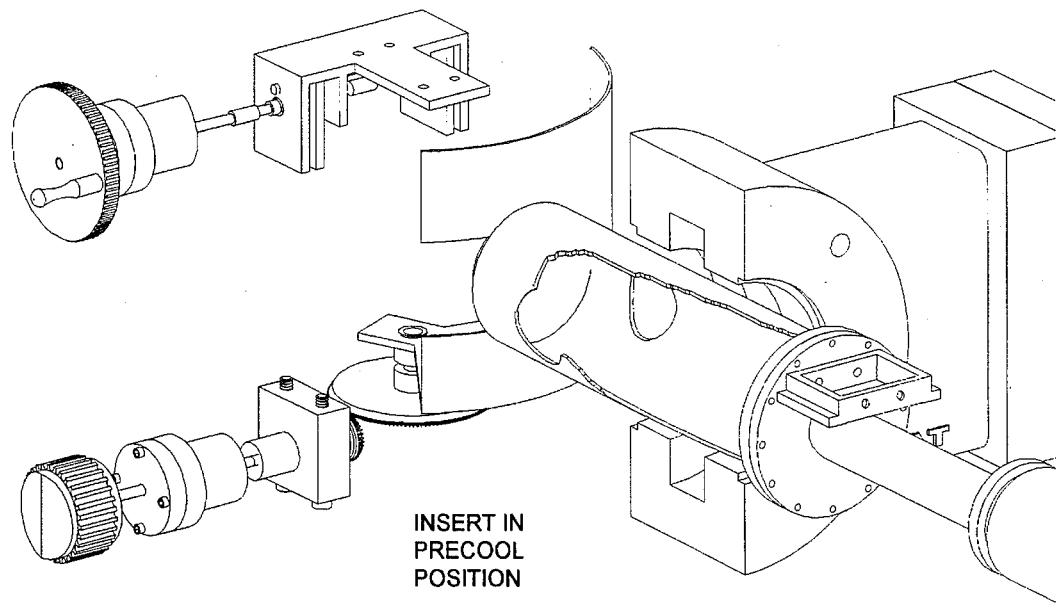
INSERT IN
PRECOOL
POSITION

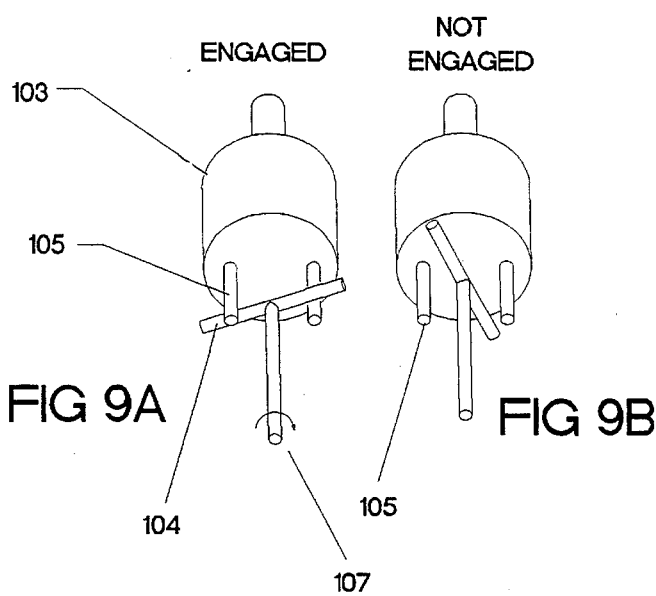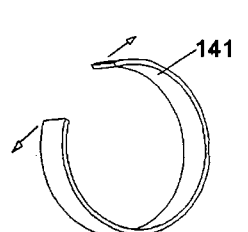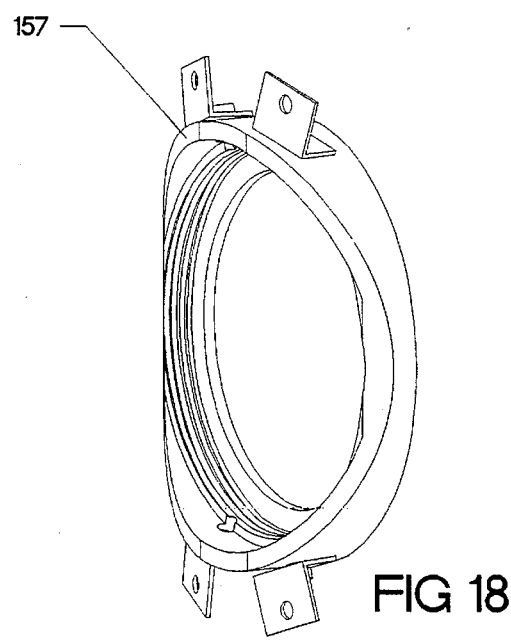

Measurement Insert

CRYOGENIC INTERFACE FOR PERPENDICULAR LOADING OF INDEPENDENT MEASUREMENT INSERTS

BACKGROUND—FIELD OF INVENTION

This invention relates to the field of measurements and investigations carded out at cryogenic temperatures.

BACKGROUND—DISCUSSION OF PRIOR ART

In many fields of research such as Experimental Physics. Materials Research, Biology or Chemistry it is often found to be desirable or necessary to cool a sample or instrumentation to cryogenic temperatures in a controlled and economical fashion. When samples are cooled, thermally induced disturbances are diminished and properties related to the atomic or molecular nature of the sample are enhanced and then are more readily investigated. Likewise when sensitive instrumentation is cooled, a variety of thermally induced backgrounds and disturbances of an electronic or molecular origin are often diminished and measurement sensitivity is enhanced.

Since cryogenic measurements are diverse and overlap many fields of science, a variety of cryogenic interfaces exists. Each variety can accommodate a certain limited range of measurements. Prior to my invention there did not exist a genuinely multipurpose interfacing solution which was able to interface an arbitrary measurement with an arbitrary cooling platform in a convenient, flexible and economical manner.

In the past manufacturers of cryogenic interfaces offered only partial solutions to the problem of designing a multi-purpose cryogenic interface. Commercial needs, until now, have been met with dedicated interfaces which satisfied only a narrow range of experimental requirements. If an experimenter wished to do a variety of cryogenic work, then it was necessary to invest in more than one cryogenic system.

A prior invention which partially achieves the objectives of a multipurpose interface between a cryogenic cooling source and an experimental sample is disclosed in U.S. Pat. No. 4,827,736 to Kazuo Miura and coworkers (1969). This patent discloses a cryogenic interface with provisions for quickly and non intrusively changing samples in an interface cooled by a Hybrid Joule-Thomson cooling source where the term hybrid refers to the precooling preceeding the J-T expansion which is provided by a Gifford-McMahon expander. The interface disclosed in U.S. Pat. No. 4,827,736 uses an on/off two position heat switch which protects the cooling source from excessive heatload during the loading cycle. A disadvantage of using an on/off type heat switch in such an interface is that no adjustment for varying experimental heat loads can be made while measurements are being carded out or while the sample is being cooled down so only a narrow range of heat loads can be dealt with without overloading the cryogenic cold source. This places a limitation on the types of cooling sources which can be used. Further limitations are that as proposed only a limited range of measurements may be carried out. There are no provisions for varying geometry and orientation of the experimental chamber.

Other prior art is represented by an effort made a number of years ago by the inventor to install a flexible quick loading system into a dilution redrigerator by leaving an open large bore vertical access tube leading to the cooling source (J. Hess and coworkers (Cryogenics, vol 17, no. 9, pp. 501–507, 1977). Variations of this method are still being used. With the present invention the disadvantages of loading large objects through large access tubes is overcome so that large objects supported by very small diameter supports may be loaded into an experimental cryostat. It is no longer necessary to tolerate the heat load of an access tube of diameter larger than the size of the object to be loaded.

OBJECTS AND ADVANTAGES

Accordingly, in the present invention experimental flexibility is enhanced by the use of independent measurement inserts which enables the loading of a full range of pre configured experiments ready for measurements rather than just the loading of a sample with limited experimental possibilities. In addition the perpendicuar loading concept provides flexibility in the orientation of the loading axis. Top loading or side loading is available as well as loading along any other direction so the geometric constraints of a variety of experimental situations can be accommodated. Further advantages of my invention over prior art include the possibility of using the full range of available cryogenic cooling sources since heat loads applied to the cyrogenic cooling source due to the loading of experiments is minimized. The low heat load also permits the use of dewars with liquid helium baths where a small helium loss rate is important.

The introduction of an easy to use multi-purpose cryogenic interface has immediate benefits for researchers working at cryogenic temperatures. The inflexibility of dedicated interfaces has had a dampening effect on researchers which discouraged the pursuit of new lines of investigation. It often happens that the effort and expense involved in refitting a cryostat for a now type of investigation is prohibitive. With a genuinely multi-purpose cryogenic interface cryogenic flexibility becomes an incentive to try now ideas. Alternatively a department engaged in diverse research projects may have had to divert resources which might have been applied otherwise, to acquiring a redundancy of cryostats and interfaces, each devoted to a particular range of measurements, when in fact a single cryogenic interface might have sufficed.

A genuinely all purpose cryogenic interface must have all of the following attributes.

1. The Interface may be used with the full range of available cryostats including closed cycle refrigerators, demand or continuous flow cryostats, dewars, hybrid J-T systems (U.S. Pat. No. 4,827,736) and thermo-acoustic coolers
2. Independent Measurement Inserts containing pre-configured experiments or measurements may be conviently interchanged one with another by scientists doing different types of measurements.
3. The cold region of the cryogenic interface must be easily accessible from any angle or orientation. In particular the Interface must provide for a quick side loading and a quick top loading capability. An air lock and precooling means provide a method for loading and unloading relatively large measurement inserts directly into and out of the cryostat vacuum without applying an undue thermal load to the cooling source. A full range of tail geometries and window materials must be readily available.
4. Variable thermal contact between cold source and Measurement Insert must be provided for a wide range of thermal impedances. This allows sensitive temperature regulation to be achieved over a broad temperature range. In addition both exchange gas and direct mechanical thermal contact must be available as thermal link options between the measurement insert body and the object to be cooled.

The perpendicular loader with independment measurement Inserts satisfies the above requirements. Still further objects and advantages will become apparent from a consideration of the ensuing description and drawings.

DRAWING FIGURES

FIG. 7 shows part of the loading cycle and details of the loading mechanism.

FIG. 9A shows the rotating shutter coupling assembly engaged.

FIG. 9B shows the rotating shutter coupling assembly disengaged.

FIG. 17 shows a springy PVC clip for retaining wires inside insert support tube.

FIG. 18 shows support into which the radiation shield extension is threaded.

Figure 1:
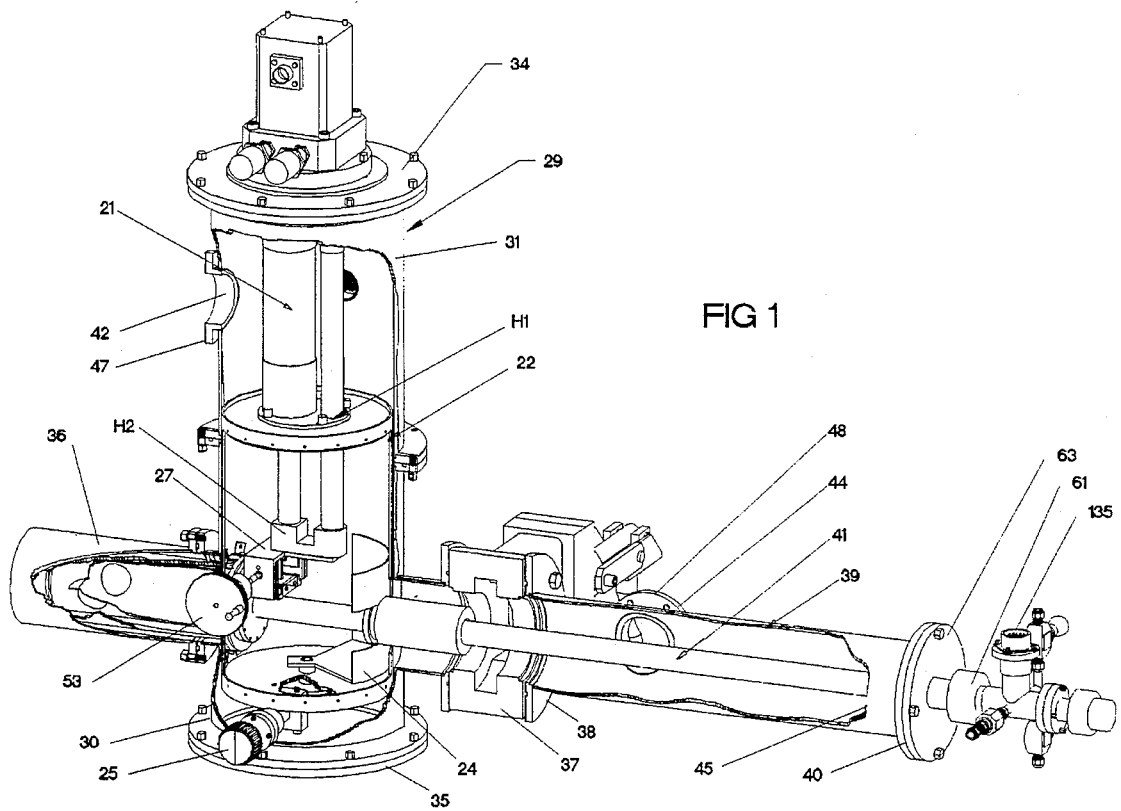
FIG. 1 is a cutaway drawing of the interface, cooled by an expander and showing a loaded insert.

| Reference Numerals In Drawings | |
|---|---|
| H1 first stage heat station | 80 threaded nut |
| H2 second stage heat station | 81 first protruding rectangular slab |
| S1 first cooling stage | 83 second protruding rectangular slab |
| S2 second cooling stage (cold stage) | 85 heatswitch body |
| 21 expander | 87 holes for heatswitch mounting bolts |
| 22 radiation shield | 91 miter gear |
| 23 circular access opening | 93 bevel gear |
| 24 rotating shutter | 95 radiation shield bottom flange |
| 25 knob | 97 shutter drive shaft |
| 27 heat switch | 99 miter gear drive shaft |
| 29 vacuum chamber | 101 bearing block |
| 30 lower vacuum chamber section | 103 coupling piece |
| 31 upper vacuum chamber section | 104 cross piece welded to end of shaft 107 |
| 34 vacuum chamber top flange | 105 off axis pin |
| 35 vacuum chamber bottom flange | 106 shutter drive coupling assembly |
| 36 demountable vacuum chamber extension piece | 107 shutter drive vacuum sealed shaft |
| 37 vacuum gatevalve | 109 shutter drive sliding O ring seal |
| 38 airlock chamber ring flange (bolted to gatevalve) | 111 heatswitch drive coupling assembly |
| 39 airlock chamber | 113 heatswitch drive vacuum sealed shaft |
| 40 airlock chamber ring flange (bolted to airlock endplate) | 115 heatswitch drive shaft |
| 41 independent measurement insert | 117 exchange gas vacuum jacket |
| 42 pump out port (welded to component 31) | 118 vacuum jacket thermal anchor |
| 44 pump out port (welded to component 39) | 119 low temperature vacuum seal |
| 45 airlock stainless steel tube | 121 1 mm O.D. indium wire |
| 47 ISO-KF-40 ring flange (welded to 42) | 123 0.5 mm deep circular groove |
| 48 ISO-KF-40 ring flange (welded to 44) | 125 circle of 2-56 NC bolts |
| 49 measurement insert base flange | 127 copper Tee |
| 51 base flange thermal anchor | 129 sliding seal asembly |
| 53 heat switch tuning knob | 131 copper Tee assembly |
| 55 intermediate stage thermal anchor | 133 0.25 inch O.D. copper tube |
| 57 measurement insert support tube | 135 heremetic feed through adapter flange |
| 61 insert tube sliding commpression seal | 137 ring flange soldered to end of support tube 57 |
| 63 airlock chamber end flange | 139 hemetic feed through connector |
| 65 access holes in measurement insert thermal anchor | 141 springy PVC wire retainers |
| 67 bolt heads | 143 insert sliding seal assembly |
| 69 stainless driveshaft | 145 insert sliding seal |
| 71 nylon guide shaft | 147 plug |
| 72 righthand threaded stainless rod | 149 vacuum valve |
| 74 lefthand threaded stainless rod | 151 vacuum valve |
| 75 welded joint | 153 check valve |
| 77 first movable copper jaw | 155 radiation shield extension |
| 79 second movable copper jaw | 157 threaded shield extension support |
| 163 sample support tube | 159 radiation shield extension cap |
| 167 liquid helium dewar | |
| 171 ac susceptibility coils | |

DETAILED DESCRIPTION OF THE INVENTION

Figure 2:
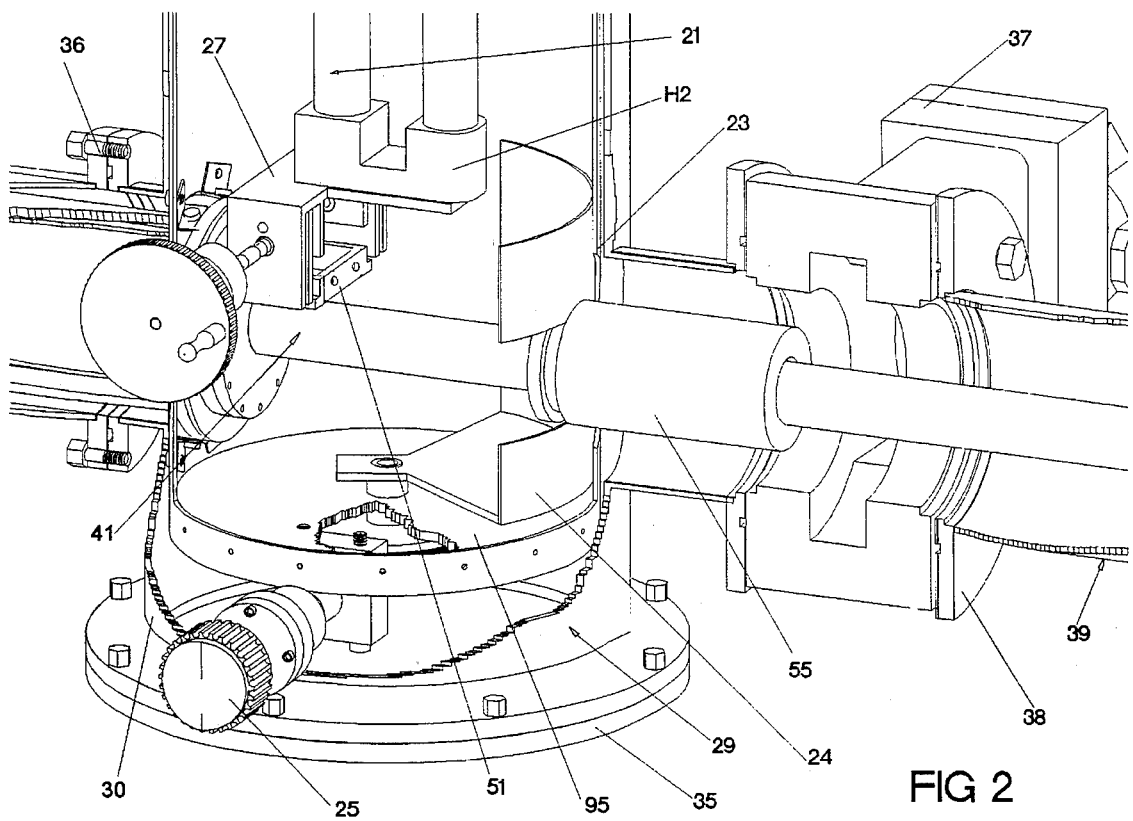
FIG. 2 is a close up view of the interface showing the insert loading mechanism.

Referring to FIG. 1 and FIG. 2, a mechanical expander 21 having first and second heat stations H1 and H2, a cylindrical radiation shield 22 thermally secured to H1 and provided with circular access opening 23, and a heat switch 27 thermally secured to H2, are enclosed in a vacuum chamber 29. The term "thermally secured" is to be taken within the context of a specific temperature range and throughout this description it refers to a low thermal impedance joint between two components which permits a relatively large heat flow to cross the thermally secured joint at a relatively low temperature differential. The first and second heat stations H1 and H2 are thermally secured to the first and second cooling stages S1 and S2 of the expander 21. The enclosed radiation shield 22 is provided with a rotating shutter 24 which rotates about the cylindrical axis of shield 22 and can be positioned by turning knob 26. All the sections of vacuum chamber 29, such as the lower and upper sections 30 and 31, are constructed from inert gas welded Type 304 stainless steel components where the welds are checked for leaks with a helium and air sensitive residual gas analyzer.

As shown in FIG. 1, the vacuum chamber 29 is bounded on top by a flange 34 upon which the expander 21 is mounted, on the bottom by a flat circular flange 35, on the right by a vacuum gate vane 37 and on the left by a demountable extension piece 36 which can be varied in design to meet particular experimental needs. All demountable vacuum joints between sections of chamber 29 are sealed in an airtight manner according to common vacuum practice using a compressible vacuum ring seal, commonly referred to as an O ring seal. When closed, vacuum gate vane 37 provides an air tight partition between chamber 29 and an air lock chamber 39 which, as shown in FIG. 1, is bolted with an O ring seal to the side of gatevalve 37 opposite to the side facing vacuum chamber 29,.

The air lock chamber 39, also shown in FIG. 1, is fabricated from a length of 3" O.D Type 304 stainless steel tube 45 and stainless steel ring flanges 38 and 40 which are welded to tube 45. The air lock chamber 39 is then vacuum checked in the same fashion as the vacuum chamber sections 30 and 31. Also shown in FIG. 1 are two pumpout ports 42 and 44 with ring flanges 47 and 48 conforming to the vacuum ISO-KF-40 (nominal 1.5 inch I.D.) standard. Pumpout port 42, located on the upper vacuum chamber section 31 is used during testing as a pumpout port or for mounting a hot filament ion gauge to measure the vacuum pressure. In ordinary use pumpout port 42 is blanked off with standard ISO-KF-40 vacuum components and only pumpout port 44 is used.

The mechanical expander 21 is operated in a closed Gifford-McMahon cycle powered by a helium compressor (not shown) and provides cooling to heat stations H1 and H2 where H1 normally operates in a temperature range from about 60 K to 100 K while H2 operates at a temperature lower than that of H1 down to a temperature of 10 K. S2, the colder of the two cooling stages S1 and S2 of the expander 21 will be designated as the cold stage. For the case of a cooling source with more than two cooling stages the term cold stage will refer to the coldest stage.

Also shown in FIG. 1 is an independent measurement insert 41 depicted with the system in the loaded position. In the loaded position gate valve 37 is open and measurement insert 41 is supported at three places, as follows.

Figure 3:
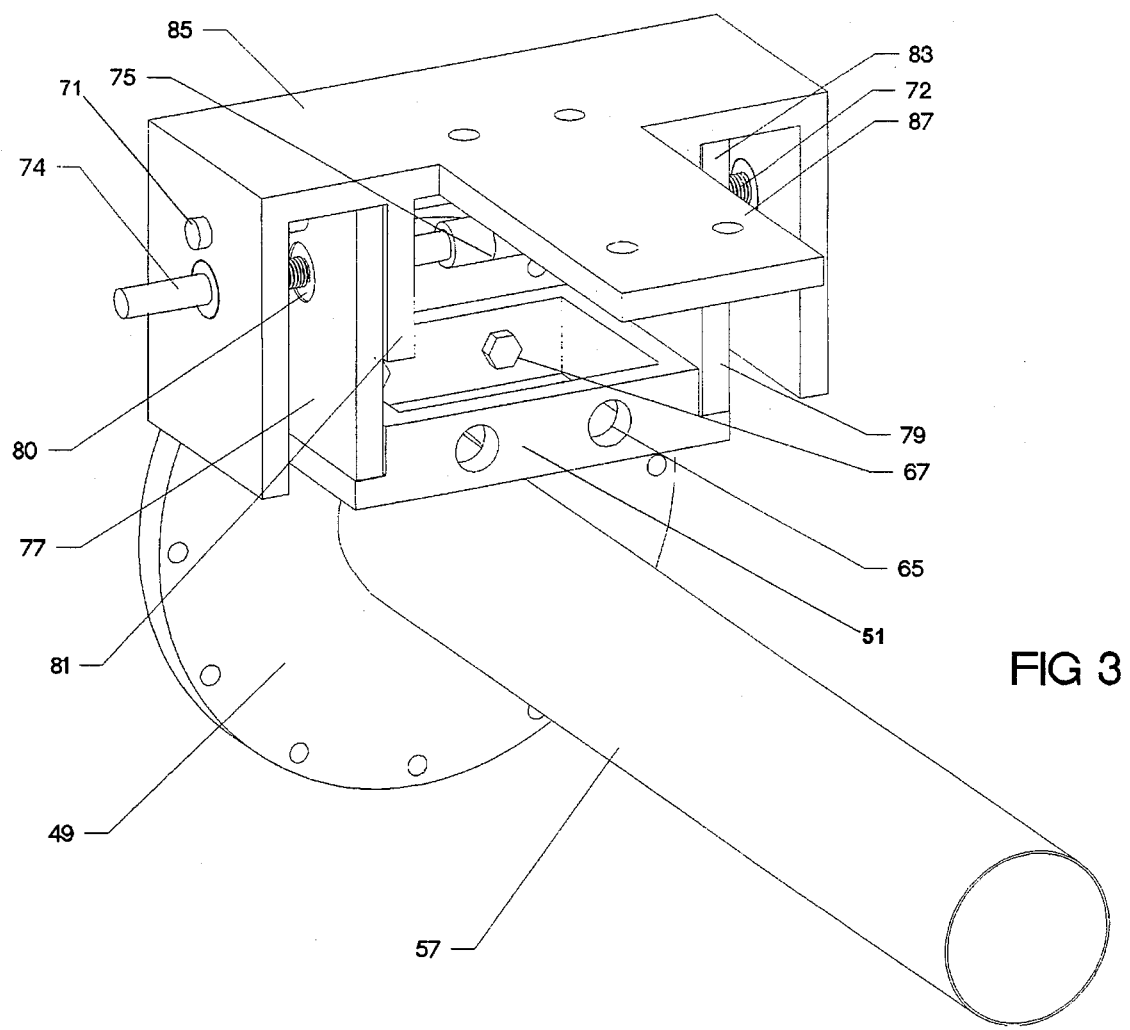
FIG. 3 shows the base flange joined to the support tube with engaged heat switch.

Firstly, inside radiation shield 22 the measurement insert is supported by heat switch 27 which is closed and engaged with a thermal anchor 51 thermally secured to the copper base flange 40 of the independent measurement insert 41. Details of the heat switch 27, which is thermally secured to heat station H2, thermal anchor 51 and copper base flange 49 are shown in FIG. 3. When heat switch 27 is engaged a thermal link of low thermal impedance is established between measurement insert base flange 49 and heat station H2 via the measurement insert thermal anchor 81. The precise value of this low thermal impedance may be adjusted by turning the knob 53.

Figure 4:
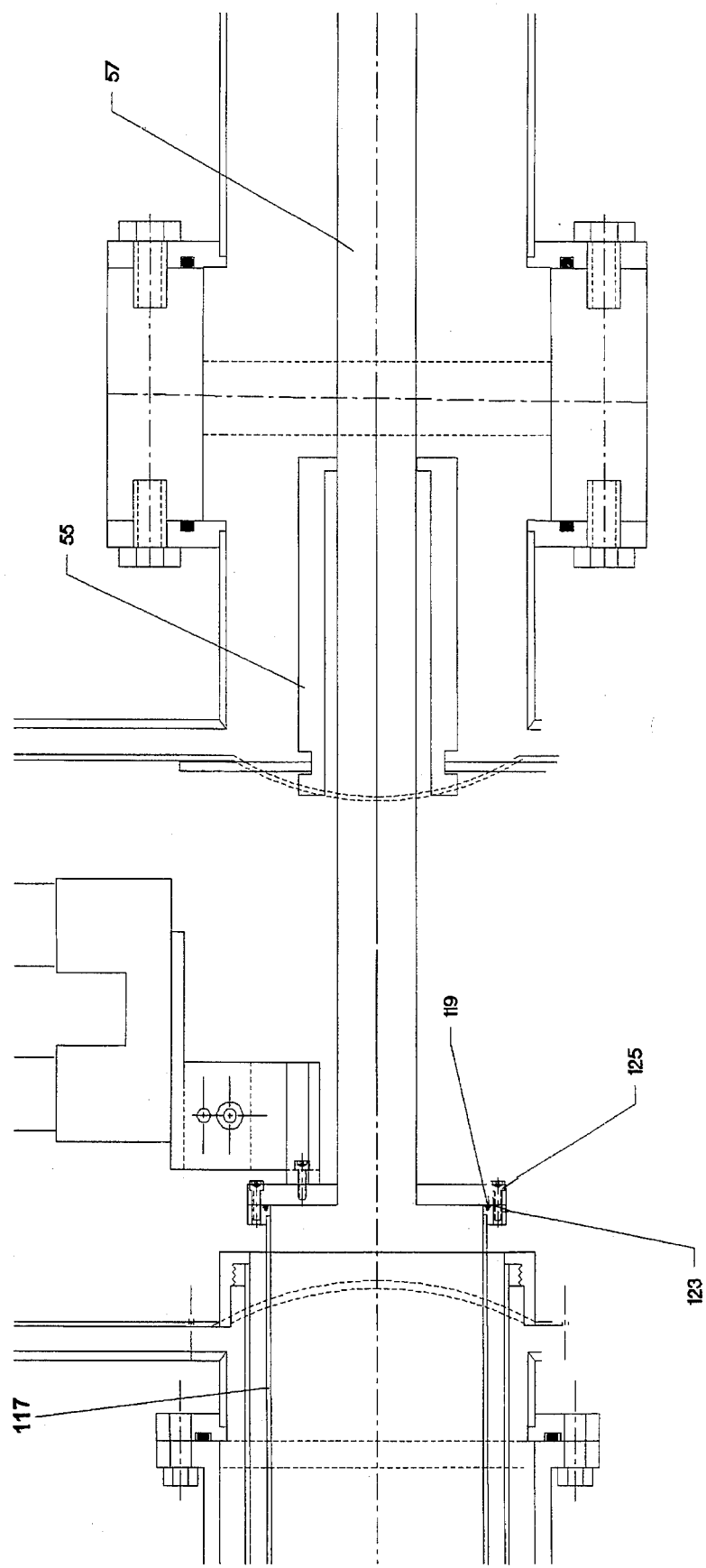
FIG. 4 shows a section view of the intermediate thermal anchor.

Secondly, as shown in FIG. 1, the independent measurement insert is supported at the radiation shield 22 by engaging rotating shutter 24 with the slotted intermediate stage thermal anchor 55. This engagement serves to establish a low impedance thermal link between the stainless steel support tube 57 and the heat station H2. By causing heat to be removed from the support tube 57 before such heat reaches heat station H2, this thermal anchoring serves to diminish the heat load applied to heat station H2 due to heat flow down the stainless support tube 57. Although a large fraction of the heat flowing through the support tube 57 which is sourced at ambient temperature is removed through the intermediate stage thermal anchor 55 there is a remaining heat flow sourced at the radiation shield 22 temperature which continues to flow toward heat station H2. This heat flow which eventually burdens the cold stage H2 can be diminished by extending the effective length of the support tube 57 between the insert base flange 49 and the hard soldered joint 87 which thermally secures the intermediate stage thermal anchor 55 to the insert support tube 57. FIG. 4 is a section view which shows how the contour of intermediate stage thermal anchor 55 has been designed so as to lengthen the section of support tube between the insert base flange 49 and the joint 87. Increasing the length of this section increases the thermal impedance between the insert base flange 49 and the joint 87 and thus reduces the the heat flow into heat station H2.

Figure 14:
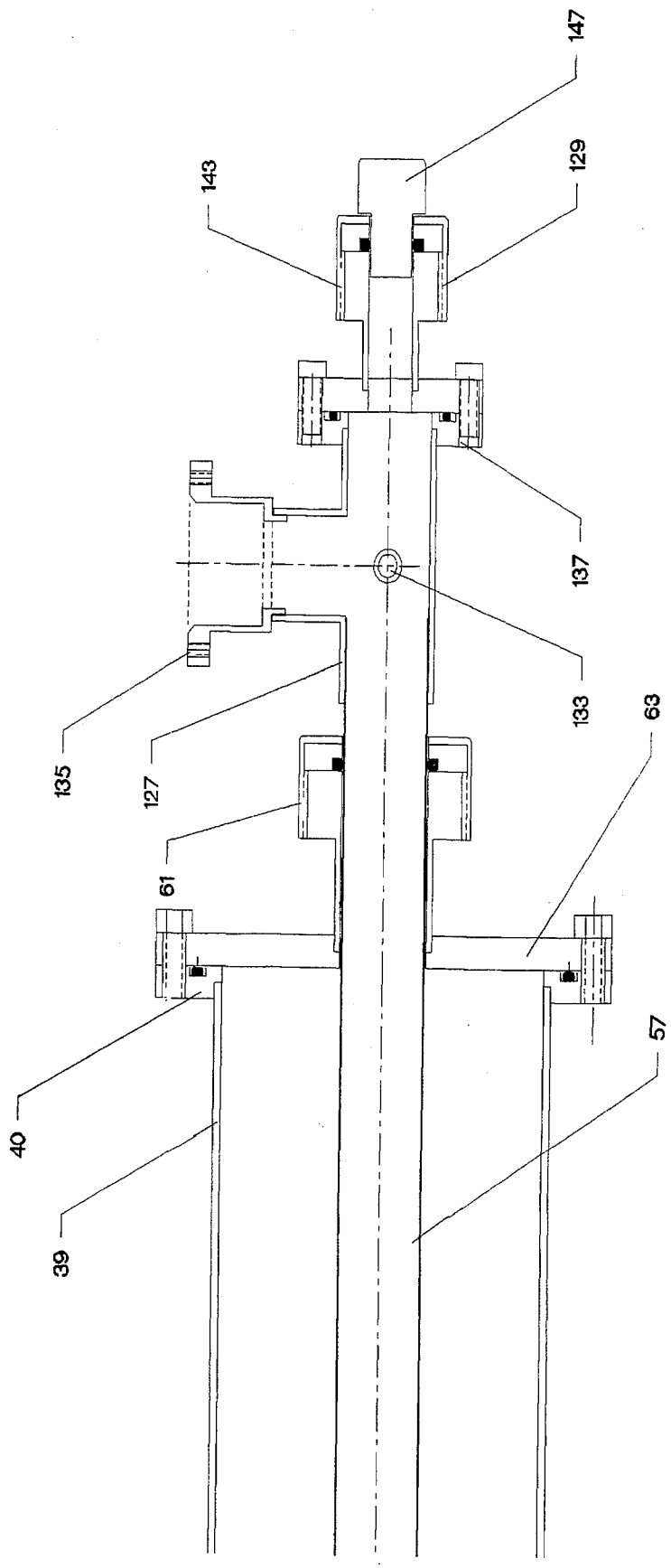
FIG. 14 shows a section view of the warm end of the measurement insert.

Thirdly as shown in FIG. 1, the warm end of the measurement insert 41 is supported by a sliding vacuum seal fitting 61 which is soldered or welded in air tight fashion to end flange 63 which is vacuum sealed to ring flange 40 of the airlock tube. A section view of the sliding vacuum seal fitting 61 is shown in FIG. 14.

Figure 6A:
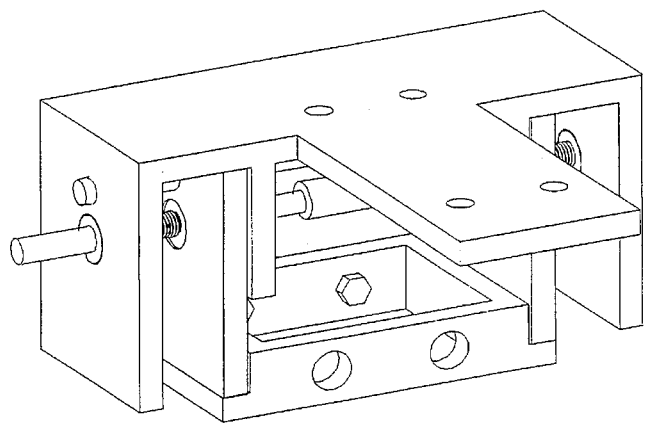
FIG. 6A shows the heat switch in the engaged position.
Figure 6B:
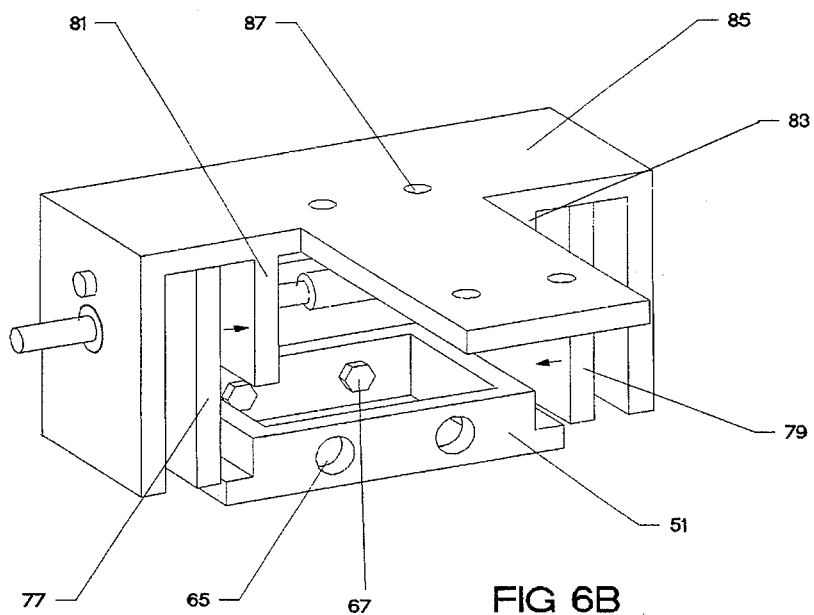
FIG. 6B shows the heat switch in an intermediate position between open and engaged.
Figure 6C:
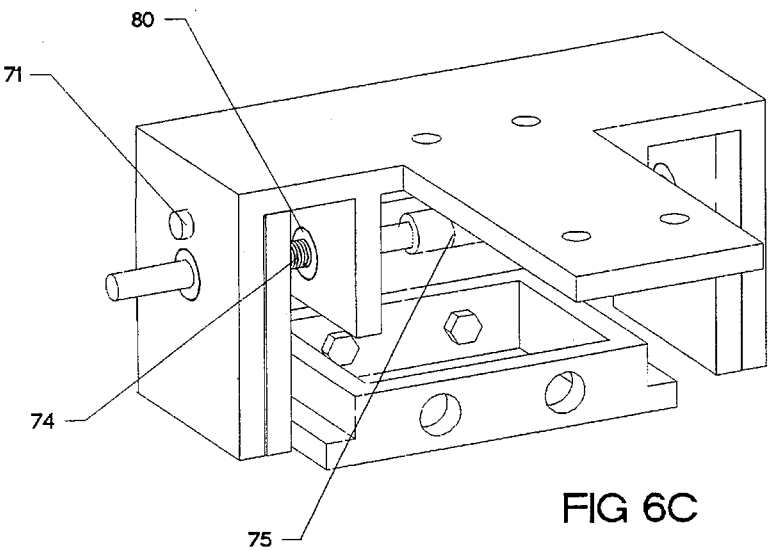
FIG. 6C shows the heat switch in the open position.

Further aspects of the heat switch 27 shown in FIG. 3 include a view of how the thermal anchor 51 is bolted to base flange 49, the stainless steel drive shaft 69 which provides lateral motion to the movable jaws 77 and 79 and the smooth nylon shaft 71 which provides alignment to the rectangular jaws 77 and 19 as they move. The shaft 69 is made from two finely threaded stainless steel rods 72 and 74 aligned and welded together at the joint 75. The stainless steel rod 72 is threaded in a righthanded sense while the stainless steel rod 74 is threaded in the opposite lefthanded sense. In the movable jaws 77 and 79 of the heatswitch 27 are imbedded nuts matching the threads of the joined stainless drive rods 72 and 74. When the shaft 69 is turned clockwise as indicated in FIG. 3 then both the movable jaws 77 and 79 move inward together and close on the matching surfaces of the thermal anchor 51. In the closed or engaged position shown in FIG. 3, a movable jaw 77 or 79 presses against a matching surface on the thermal anchor 51 and also a parallel matching surface on one of the protruding rectangular slabs 81 or 83 which are part of the heatswitch body 85 which is machined from a single piece of OFHC high conductivity copper. By pressing simultaneously against the parallel surfaces of the protruding slabs 81 or 83 and the matching parallel surfaces of the thermal anchor 51 the moving jaws 77 and 79 achieve good thermal contact between the thermal anchor and the heatswitch body 85, even at the lowest operating temperatures below 10 K. In actual operation the matching copper contact surfaces of the heatswitch 27 may over time accumulate a thin oxide coat. For optimum performance of the heat switch 27 it is then necessary to lightly clean the matching surfaces with copper polish. Also shown in FIG. 3 are four through holes 87 in the top surface of the heatswitch body 85. These holes are for bolts which thermally secure the heatswitch body 35 to the second stage heat station H2. The two holes 65 in thermal anchor 51 which appear in this view provide access to the bolt heads 67 so that they may be secured with a wrench. A sequence of heat switch views FIG. 6A, FIG. 6B and FIG. 6C show the heat switch in engaged position, in an intermediate position and in the open position. In the open position where access is provided for the base flange of the independent measurement insert 41 during the loading operation. The loading and unloading processes are described in detail further on.

Figure 8:
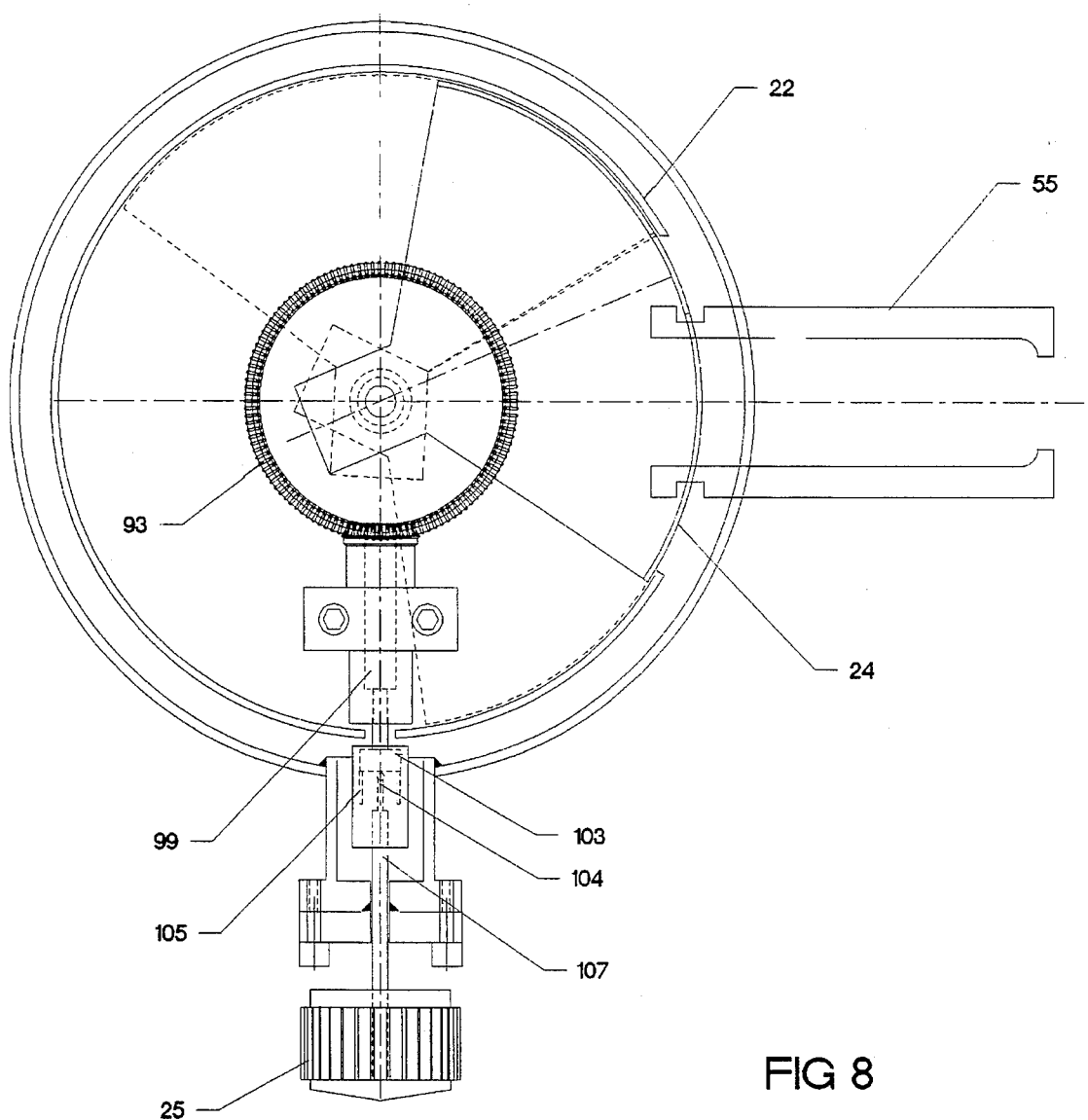
FIG. 8 shows plane view of radiation bottom with bevel gear looking up.

Additional details of the radiation shield 22 and the rotating shutter 24 shown in FIG. 7 and FIG. 8 include a 30 tooth miter gear 91 and a 120 tooth bevel gear 93 matched set where bevel gear 93 is mounted mounted on the down side of the radiation shield bottom flange 95 on the shutter drive shaft 97. The shutter drive shaft 97 passes through the radiation shield bottom flange 95, which is not shown in FIG. 7. The matched miter gear 91 is mounted on stainless steel shaft 99 supported by bearing block 101. On the end of shaft 99, opposite to the end with the miter gear 91, is mounted a coupling piece 103 with two off axis pins 105 projecting from it parallel to the shaft 99. Along the axis defined by shaft 99 is another stainless steel matching shaft 107 which can be rotated and longitundinally displaced in the sliding O ring seal 109 which is welded in a leak free fashion to the to the vacuum chamber 29. The shaft 107 can thus transmit rotary and longitudinal motion through the wall of the vacuum chamber 29. Referring to FIG. 8, on the end of the shaft 107 facing the coupling 103 is welded a cross piece 104 like the horizontal cross piece of the letter T. The cross piece 104 and the coupling piece 103 with pins 105 comprise the coupling assembly 106. On the end of shaft 107, outside the vacuum chamber 29, is mounted a knurled knob 109. When it is desired to transmit rotary motion to the rotary shutter, the shaft 107 is displaced longitudinally and rotated with knob 109 until the crosspiece 104 engages the pins 105 of the coupling piece 103 as shown in FIG. 9A. With the crosspiece 104 engaged with the pins 105 rotaty motion of the shaft 107 is transmitted to shaft 99 and then via the miter and bevel gear matched set 91 and 93 to the rotating shutter 24. When a final position has been selected for the rotating shutter 24, thermal contact between the shafts 99 and 107 is broken by turning the shaft 107 back 90 degrees from the engaged position shown in FIG. 9A to the disengaged position shown in FIG. 9B. In the disengaged position there is no heat flow from the warm sliding O ring seal 109 to the coupling piece 103 which has a low thermal conductance path via the rotating shutter 24 and radiation shield to the first stage heat station H1 of the mechanical expander 21. This arrangement then prevents excessive heat load to fall upon on the expander first stage S1 when the rotating shutter 24 is not being moved.

A similar fork type coupling assembly 111 similar to 106 is used to transmit rotation from the knob 53 and vacuum sealed drive shaft 113 to the drive shaft 115 which activates the heat switch 27. Coupling assembly 111 is shown in FIG. 7. In a fashion identical to the operation of the coupling assembly 106, the coupling assembly 111 thermally disconnects the heat switch 27 from the warm drive shaft 113 when the heat switch is not being operated. By breaking the thermal contact between the heatswitch 27 and drive shaft 113, heat flow sourced at ambient temperature to the cold stage of the expander 21 is interrupted.

Figure 10:
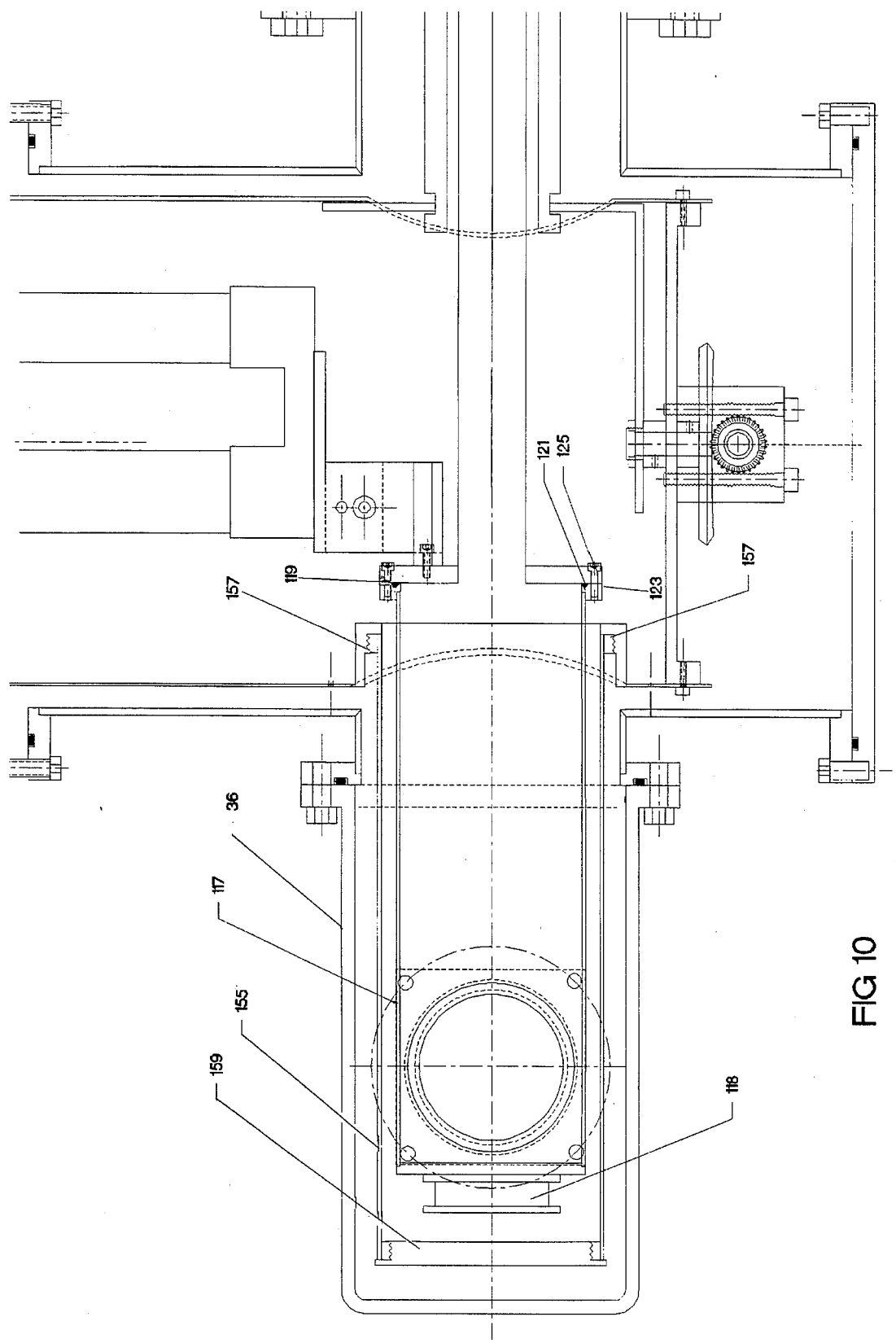
FIG. 10 shows a section view of the exchange gas vacuum jacket and associated components.
Figure 13:
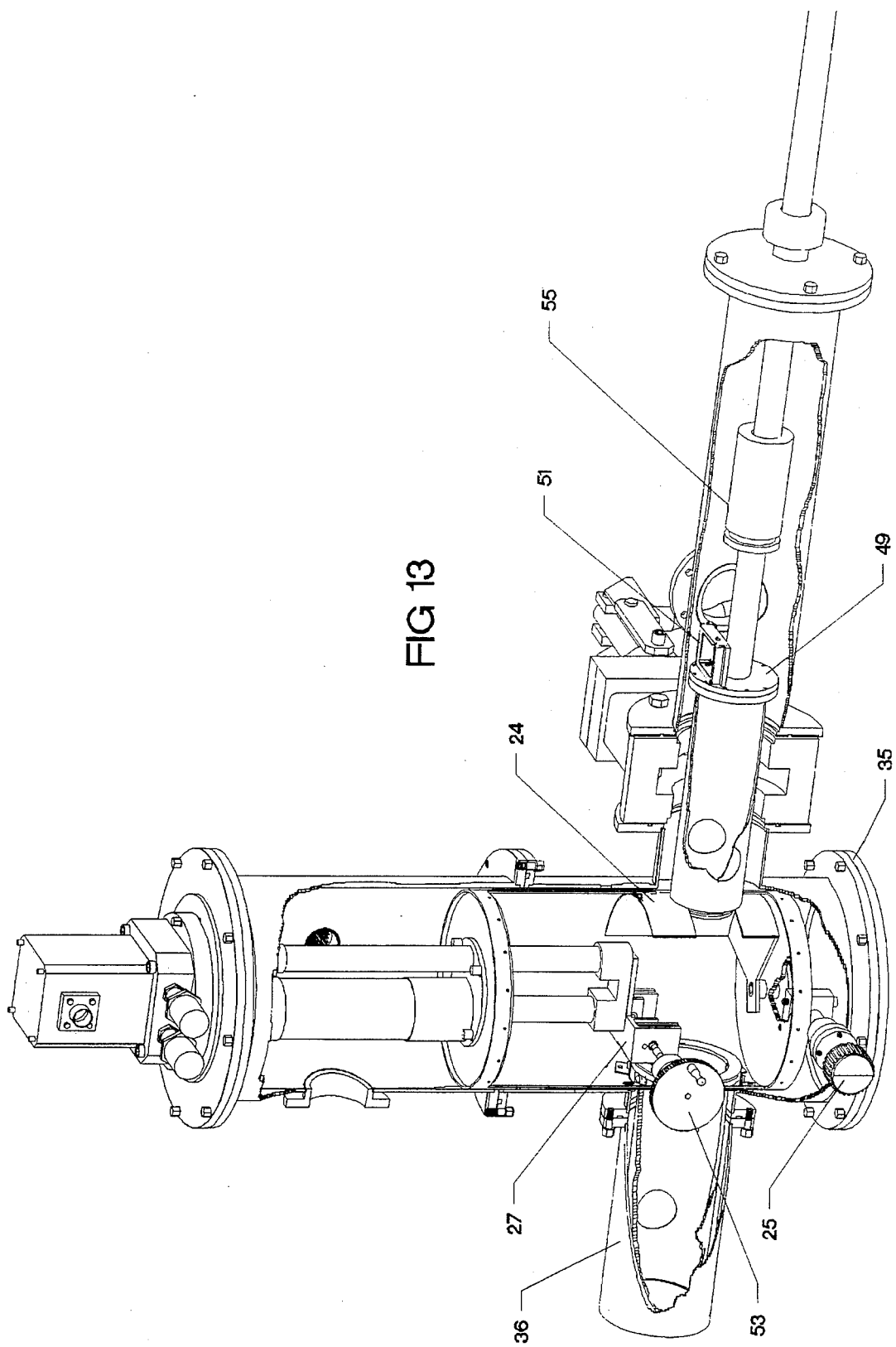
FIG. 13 shows the insert pre cooling pad of the loading cycle.

Static features of the independent measurement insert 41 which remain to be described include the exchange gas vacuum jacket 117 which is bolted to the measurement insert base flange 49 when the measurement insert 41 is to be filled with exchange gas and also the components and fittings which are attached to the warm end of 41. The purpose of filling the measurement insert 41 with exchange gas is to provide a gaseous thermal link from the base flange 49 and exchange gas jacket 117 to an object within 117 which is to to be cooled. Reasons for the application of exchange gas thermal coupling include a sometimes need to vibration isolate an object to be cooled from the vibrations of expander 21 or to provide an experimental thermal link which is not electrically conducting. A section view of the exchange gas jacket is shown in FIG. 10 and a three dimensional view is shown in FIG. 13 where the vacuum jacket thermal anchor 118 is shown engaged with the shutter 24. The vacuum seal 119 which secures the vacuum jacket 117 to the base flange 49 is fashioned from a ring 1 mm diameter indium wire 121 placed in a .05 mm deep circular groove 123 just within a circle of 2–56 NC bolts 125. The indium ring is made from indium wire which is pushed into the circular groove and spliced to form a continuous ring by simply letting the ends overlap inside the circular groove 123 in such a way that the overlap will be compressed when the securing bolts 125 are tightened. On tightening the bolts 125 which secure the exchange gas jacket 117 to the base flange 49 the soft indium metal ring is compressed and flows out of its restraining circular groove 123 to spread over the surfaces adjacent to the groove 123. If there are no radial scratches on the sealing surfaces close to groove 123 then the indium metal vacuum seals the adjacent copper surfaces of the exchange gas jacket 111 to the base flange 41 in a manner that withstands temperature cycling from ambient temperature to the lowest operating temperatures.

Figure 15:
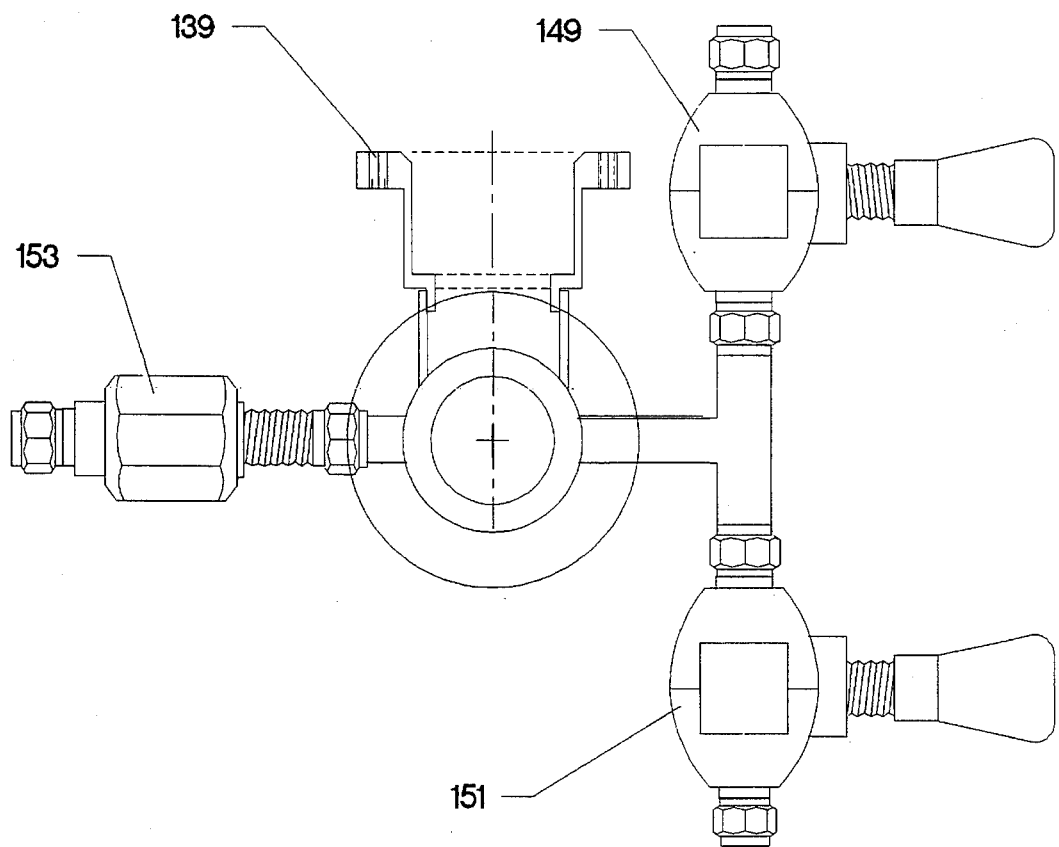
FIG. 15 shows an end view of the measurement insert looking toward the gatevalve.
Figure 16:
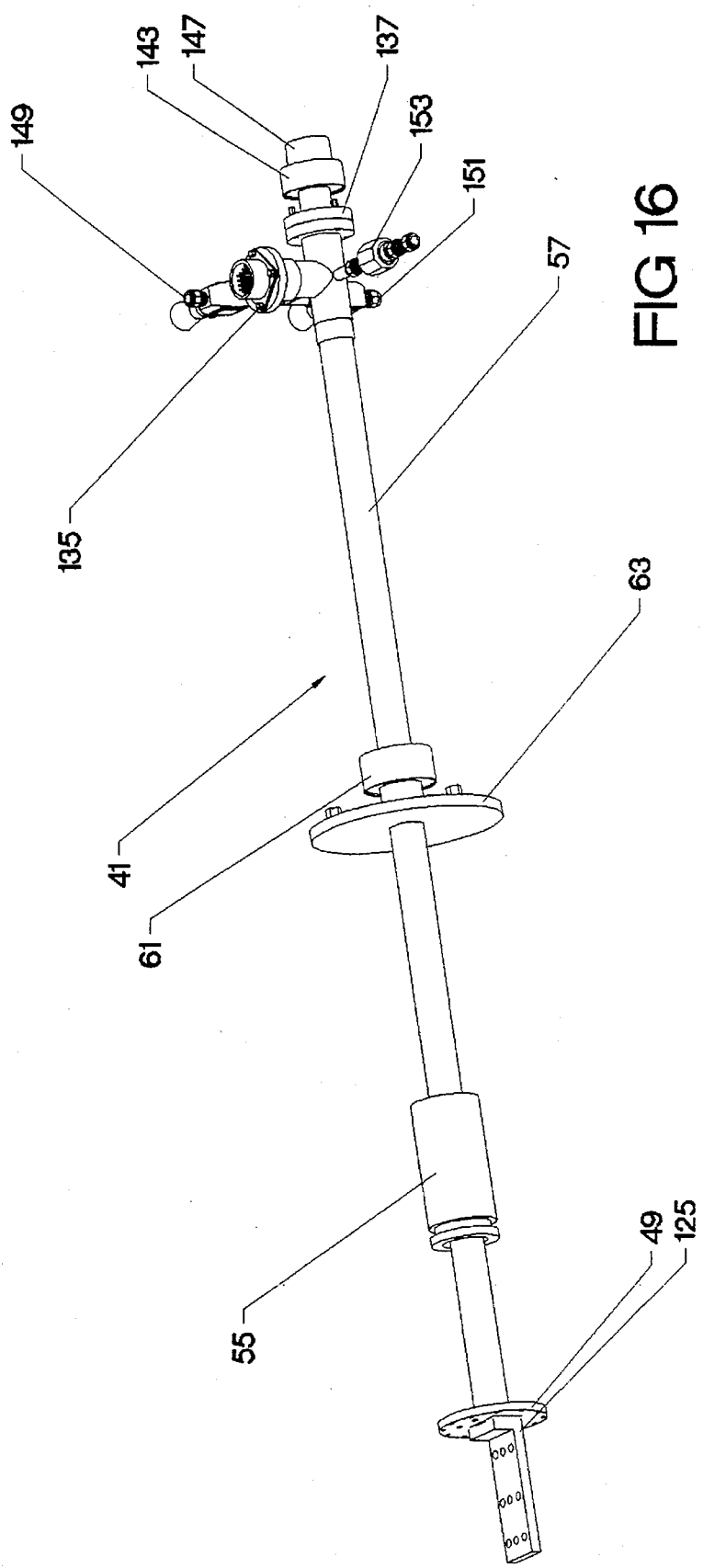
FIG. 16 shows a three dimensional view of the measurement insert with copper heat link.

Details to be described below, of the warm end of the independent measurement insert 41, are shown in the plane views of FIG. 14 and FIG. 15 and in a three dimensional view in FIG. 16. The warm end of the measurement insert 41 is terminated by a copper Tee solder fitting 121 which is hard soldered to the measurement insert support tube 57. Prior to completing the basic insert 41 assembly by soldering the base flange 49 and the copper Tee 127 to the insert support tube 57 the sliding seal assembly 129 consisting of airlock end flange 63 and sliding compression seal 61 with O ring must be completely assembled onto the insert support tube 57. The copper Tee assembly 131 is completed by hardsoldering a 0.25 O.D. copper tube 133 into a sliding fit 0.25 diameter hole drilled into copper Tee 127 and at the same time hardsoldering an adapter flange 135 onto the center leg of the Tee 127 as well as a ring flange 137 with O ring groove onto the leg of Tee 127 opposite to the leg which is hardsoldered to the support tube 57. Into the adapter flange 135 a hermetic feed through connector 139 is O ring sealed sealed. This connector 139 is part of the independent experimental wiring provisions of the measurement insert 41 and in operation is connected to a mating external connector. Wiring for experiments extends down the inside of the support tube 57 through the opening in the base flange 49 into the cooled experimental region inside the exchange gas jacket 117. Springy circular segments 141, cut from a PVC tube and shown in FIG. 17, are inserted inside the support tube 57 after the wiring is installed to keep the wiring snugly pressed against the inside wall of the support tube and and protected. This is important for applications described further on where experimental samples are quick loaded down the support tube 57.

The ring flange 137 provides for another sliding seal assembly 143 with sliding seal 145 to be sealed with an O ring to the end of the support tube 57. When not in use the sliding seal 145 is sealed with a vacuum tight plug 147. Finally with the aid of another 0.25" copper Tee ring, the copper tube 133 is used to mount two vacuum valves 149 and 151 and a check valve 153 which opens from the inside at ⅓ psi positive and acts to assure that when exchange gas is used no large internal exchange gas pressures develop due to the large temperature swings of the cooled part of the independent measurement insert 41. The two vacuum valves 149 and 151 and the check valve 163 are mounted on 0.25 inch O.D. copper tube with standard vacuum rated compression fittings. The two valves 149 and 151 are used when exchange gas is used for pumping out and backfilling the the independent measurement insert 41.

To complete the isolation of the cold stage S2 from thermal radiation sourced at ambient temperature it is necessary to extend the radiation shield in such a way that it envelops the exchange gas jacket 111 of the measurement insert 41. This is so since in the loaded position the jacket 117 has a direct thermal link through base flange 49 and the engaged heat switch 27 to the cold stage S2. A section view of the radiation shield extension 155 which shields the vacuum jacket 117 is shown in FIG. 10. It is secured in the radiation shield 22 with a thread which screws into a matching threaded piece 157, shown in FIG. 18, which is thermally secured to the radiation shield. Since the radiation shield 22 is disposed within the commom vacuum space of the vacuum chamber 29, there is no need to vacuum seal 157 to the radiation shield 22. A good thermal joint is sufficient. At the outer end of the radiation shield extension 155 is a threaded cap 159 which during assembly may be removed to check mechanical alignment of the loaded insert 41.

Figure 19:
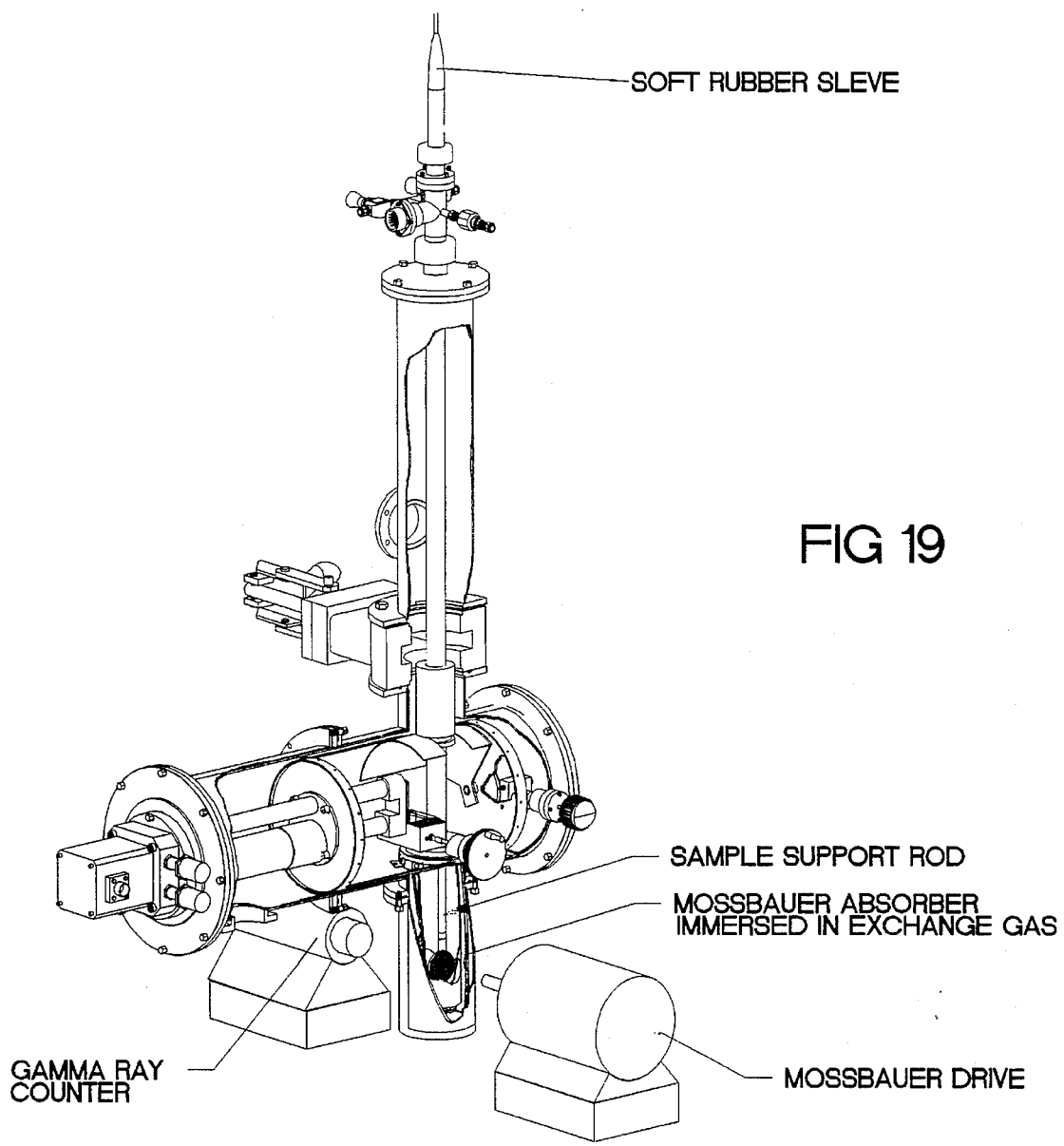
FIG. 19 shows the interface oriented for top loading to perform Mossbauer Effect measurements.
Figure 20:
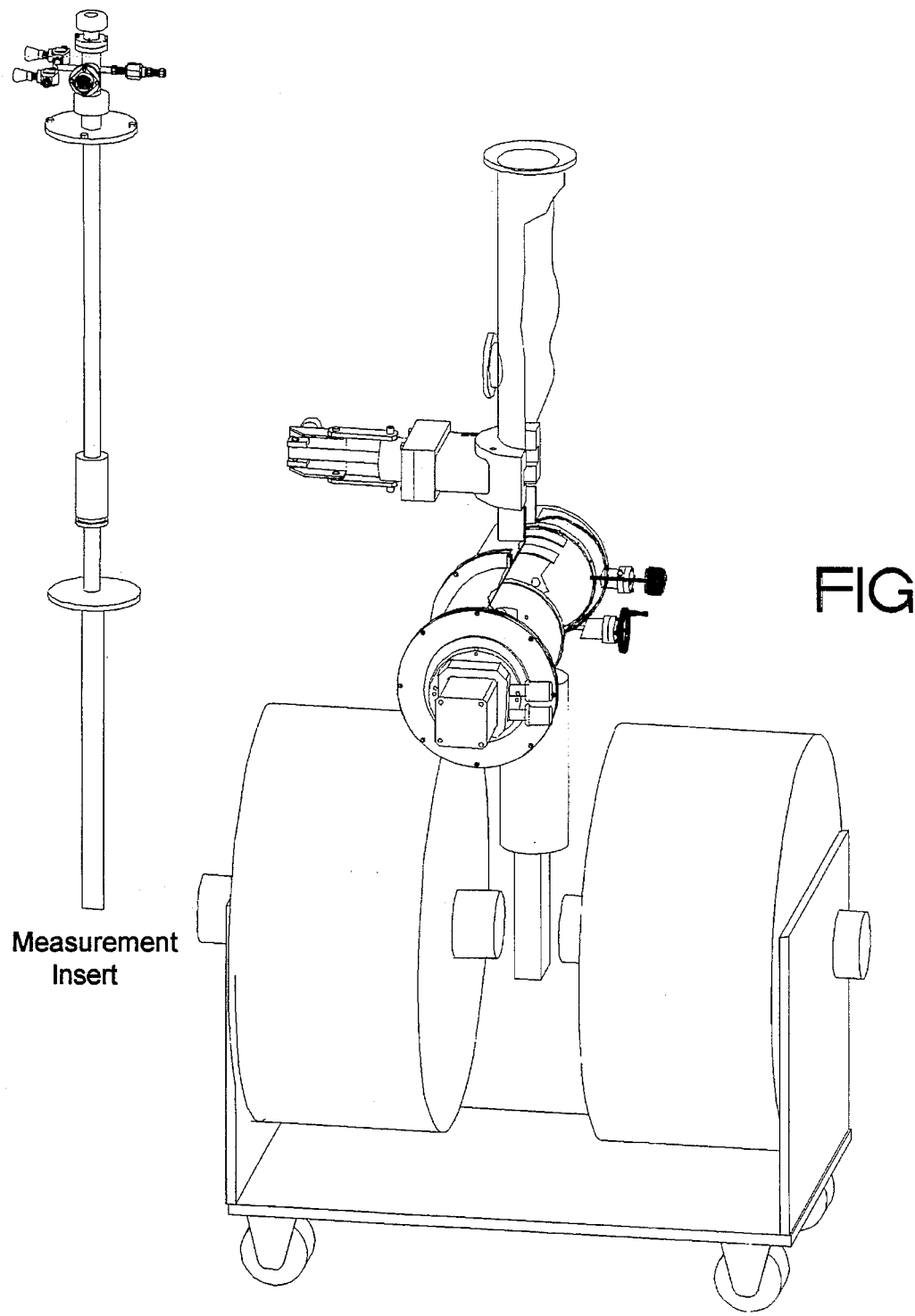
FIG. 20 shows the interface oriented for top loading to perform EPR measurements in a magnet.

Two final remarks complete the static description of the invention. The first final remark is that for some cooling sources low thermal conductance spacers 161 made of nylon or a similar low thermal conductance material should be inserted between the radiation shield bottom flange 95 and the inner wall surface of the lower vacuum chamber section 30 when the interface is to be used with a top loading orientation as shown in FIG. 19 and FIG. 20. For some G-M expanders or cryostats using a spilless liquid helium bath, the turning moment applied by the radiation shield top flange to the first stage S1 of the cooling source might be sufficient to cause distortion when the cryostat is oriented along a horizontal axis. To make the structure sufficiently sturdy for every day laboratory use it may be necessary to insert low thermal conductance spacers 161, as shown in FIG. 8.

The second final remark is that the lower vacuum chamber section 30 is a stainless steel cross fabricated from a 6 inch O.D. tube reducer cross where the two cross arms of smaller O.D. along which the independent measurement insert 41 is loaded are fabricated by extruding or "popping out" short sections of the appropriate diameter to which standard tube extensions are then machine welded. Such "popped out" crosses are available from the major vacuum component manufacturers. In this context it should be noted that such reducer crosses are available with cross arms of up to 5 inch diameter so that a 5 inch I.D. airlock chamber with appropriately enlarged gate valve can be used to perpendicular load objects requiring a four inch access diameter. The advantages of the perpendicular loading system are still retained with this modification so that very large objects can be loaded with independent measurement inserts 41 having small cross section support tubes 57 so that the heat load on the cold stage can still be kept under 10 mW. This is particularly useful if a cold source using a liquid helium bath is used since the liquid helium bath boil off rate can be kept well under one liter per day with a loaded independent measurement insert in place. Such a low boil off rate is not attainable using conventional prior art loading systems.

Operation of the Invention

A general loading sequence common to all operating modes and experimental configurations is as follows. An airlock punping vane conforming to the ISO-KF-40 vacuum standard is mounted on the ring flange 48 and is used to pump out or vent the airlock chamber 39 as required. The steps of the general loading sequence are depicted FIG. 11, FIG. 12, FIG. 13, FIG. 1 and FIG. 2.

Figure 11:
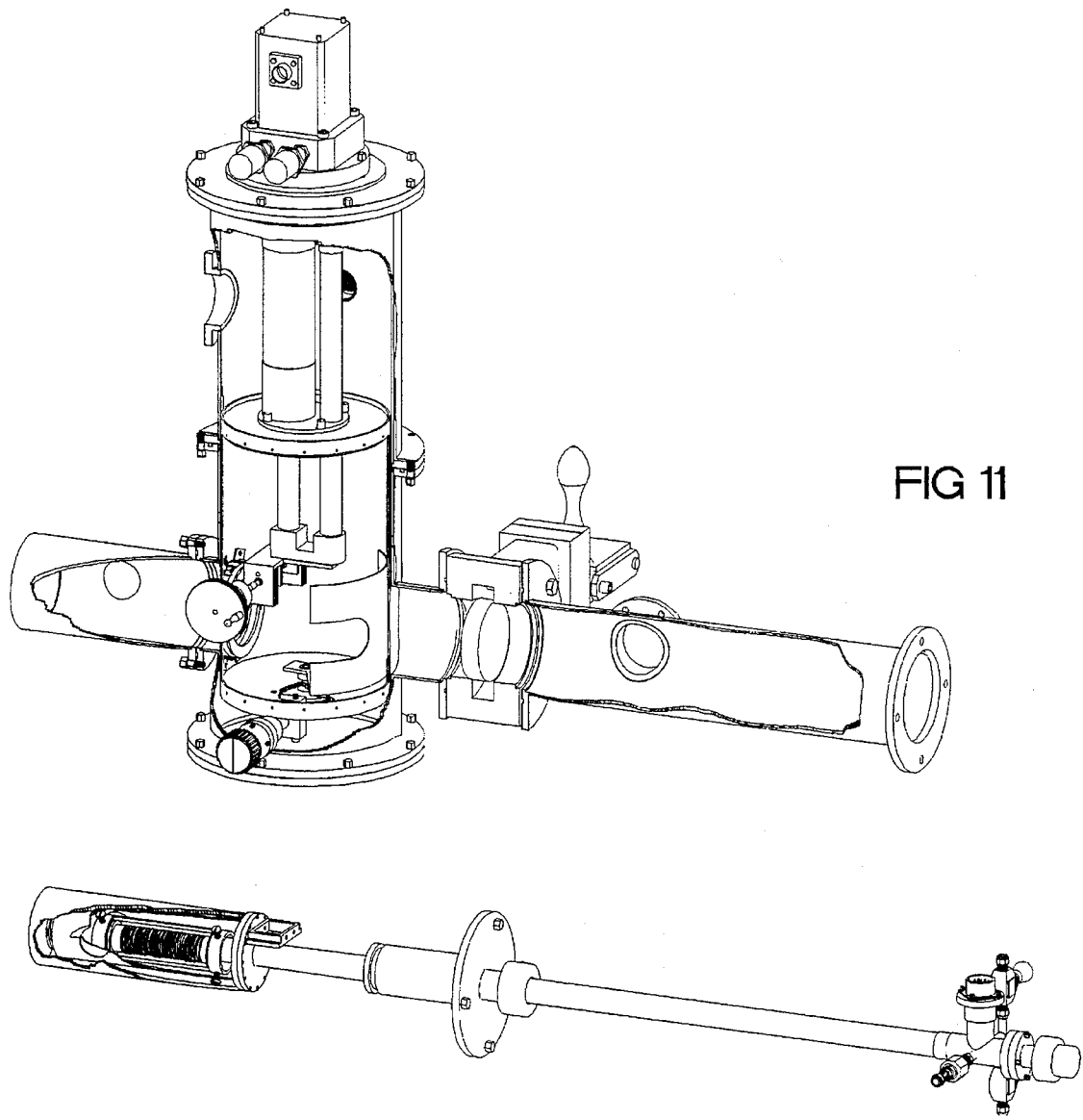
FIG. 11 shows and interface with unloaded independent measurement insert.
Figure 12:
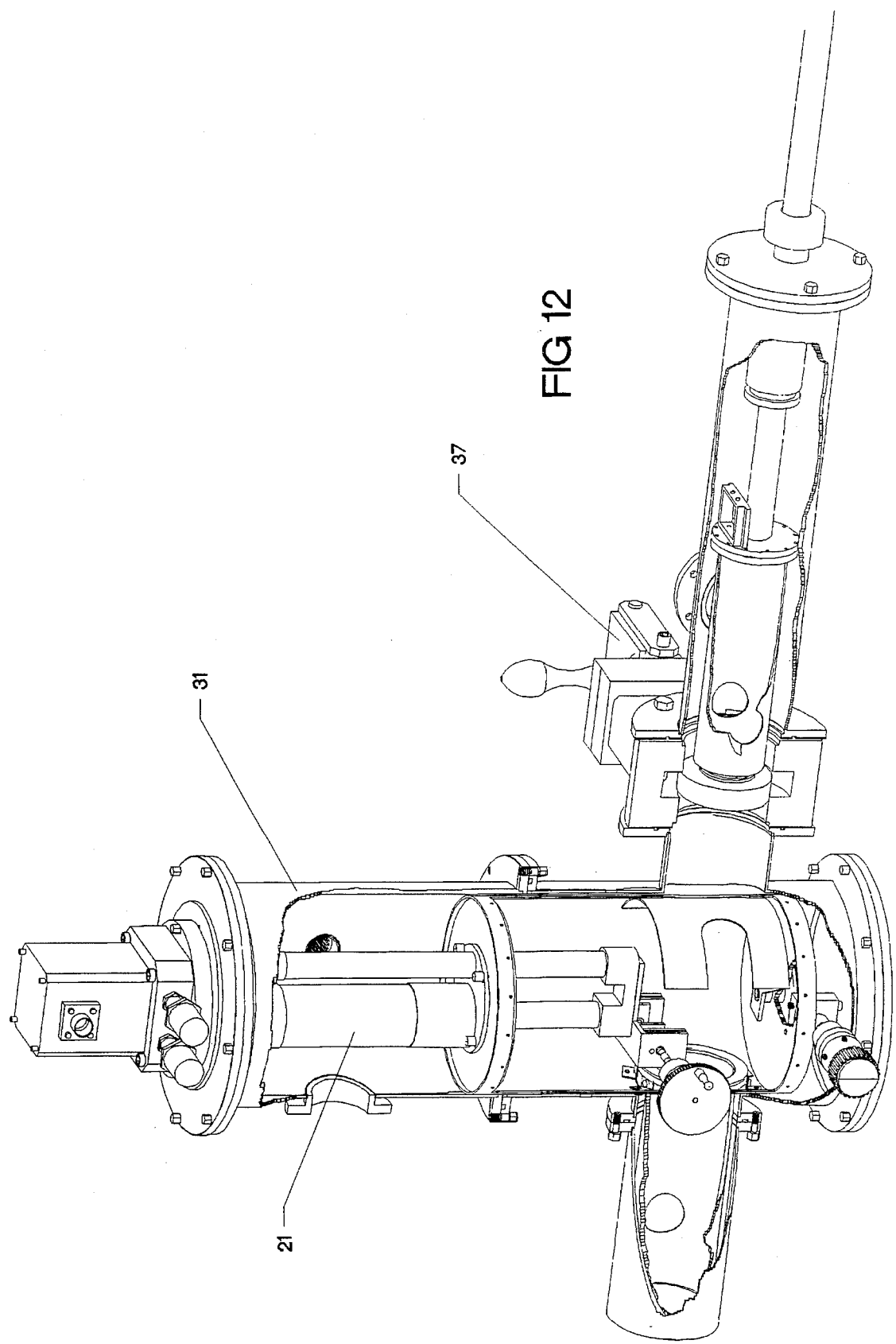
FIG. 12 shows an independent measurement insert loaded into the airlock.

(a) With vacuum gatevalve 37 and rotating shutter 24 closed, bolt airlock end flange and measurement insert support 63 to airlock ring flange and pump airlock chamber 39 down to a thermally insulating vacuum. Refer to FIG. 11 and FIG. 12.

(b) Open vacuum gatevalve 37 and rotating shutter 24, advance independent measurement insert 41 through insert tube compression seal 61 and engage vacuum jacket thermal anchor 118 in notch of rotating shutter by partially closing the rotating shutter 24. Refer to FIG. 13.

(c) When the heat content of the cold end of the independent measurement insert 41 falls below a level which can readily absorbed by the cryogenic cooling source with only a short term disruption of the cryogenic cooling source operating point, reopen rotating shutter 24, further advance independent measurement insert through compression seal 61 and then engage intermediate stage thermal anchor 55 with rotating shutter 24. Refer to FIG. 1 and FIG. 2.

(d) Engage heat switch 27 with base flange thermal anchor 51 of independent measurement insert 41 and adjust thermal impedance between independent measurement insert 41 and cold stage S2 to value appropriate to the operating temperature of said independent measurement insert 41. Refer to FIG. 1 and FIG. 2.

Similarly, a general unloading sequence common to all operating modes and experimental configurations is as follows:

(a) Disengage heat switch 27 with base flange thermal anchor 51 of the independent measurement insert 41.

(b) Reopen rotating shutter 24 and withdraw independent measurement insert 41 through compression seal 61 until cold end of independent measurement insert 41 is entirely within the airlock chamber 39.

(c) Close rotating shutter 24 to shield cold stage S2 from thermal radiation sourced at ambient temperature.

(d) Close vacuum gate vane 37 and vent airlock chamber 39 with fast opening and closing of airlock pumping vane to ambient air pressure so as to admit a fraction of an atmosphere of air into airlock 39. Venting airlock 39 in this manner will admit insufficient moisture for condensing rater on cold end of independent measurement insert 41 but will still allow insert to warm up rapidly.

(e) When insert 41 reaches ambient temperature, unbolt bait airlock end flange and measurement insert support 63 and remove independent measurement insert 41 from airlock chamber.

Ramifications and Scope

FIG. 19 and FIG. 20 show the perpendicular loader oriented for top loading experiments. Until now the side loading orientation has been used for illustrative purposes, however having the option to orient the interface loading axis in any direction convenient for a particular experiment is an important feature of the present invention and adds a new measure of flexibility to interface design.

FIG. 19 uses the top loading orientation for a Mossbauer Experiment such as discussed in U.S. Pat. No. 3,894,403 to Longsworth. In the present invention the vibration isolation dicslosed is significantly simplified and samples may ba changed with a quick loading procedure that does not even require the unloading and loading of the measurement insert 41. With a somewhat enlarged insert support tube 57 a Mossbauer sample may simply ba supported by a thin wall stainless steel sample support tube 163 and loaded directly into the insert support tube 57. The sample support tube 163 is then aligned in such a way that there is no contact between it or the sample with the measurement insert 41. The measurement insert 41 is filled with helium exchange gas and a soft rubber sleeve is used to create a seal between an extension tube which is secured to the insert ring flange 137 and the sample support tube 163. The sliding seal assembly 143 is not used in this case. It turns out that to achieve good vibration isolation with this arrangement, only the sample support tube and the Mossbauer drive must ba rigidly supported. With the interface disclosed in U.S. Pat. No 3,894,403 to Longsworth, the entire interface must be rigidly supported and aligned.

FIG. 20 shows a top loading arrangement used to access the narrow gap of a large electromagnet such as is used in an EPR (electron paramagnetic resonance) experiment. A narrow geometry version of the demountable vacuum chamber extension piece 36 is used for this application as well as a matching narrow geometry version of the radiation shield extension. For this application no exchange gas and no exchange gas vacuum jacket 117 is used. Instead a configuration of the type shown in FIG. 16 is used where thermal contact with the insert base flange 49 is established with a copper sample support 165 which bolts directly to the insert base flange 49. For sample loading the measurement insert is directly loaded into the vacuum chamber 29 as described above. No indium seal is used in this case since no exchange gas vacuum jacket 117 is used.

Figure 21:
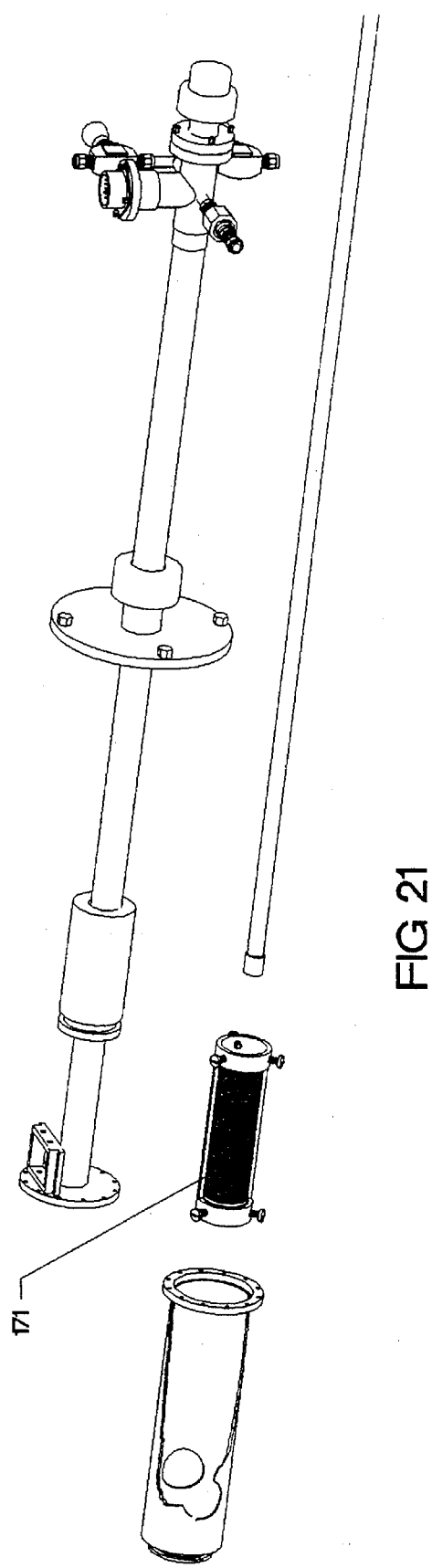
FIG. 21 shows measurement insert configured for ac susceptibility measurements.

FIG. 21 shows another measurement insert configuration used for AC magnetic susceptibility measurements. A small sample is directly loaded into the exchange gas filled exchange gas vacuum jacket 117 with a sample support tube. In this appplication the sliding seal assembly 143 is used to seal the sample support tube. FIG. 21 also shows AC magnetic susceptibility coils 171 which fit into the cylindrical exchange gas vacuum jacket 117.

Figure 22:
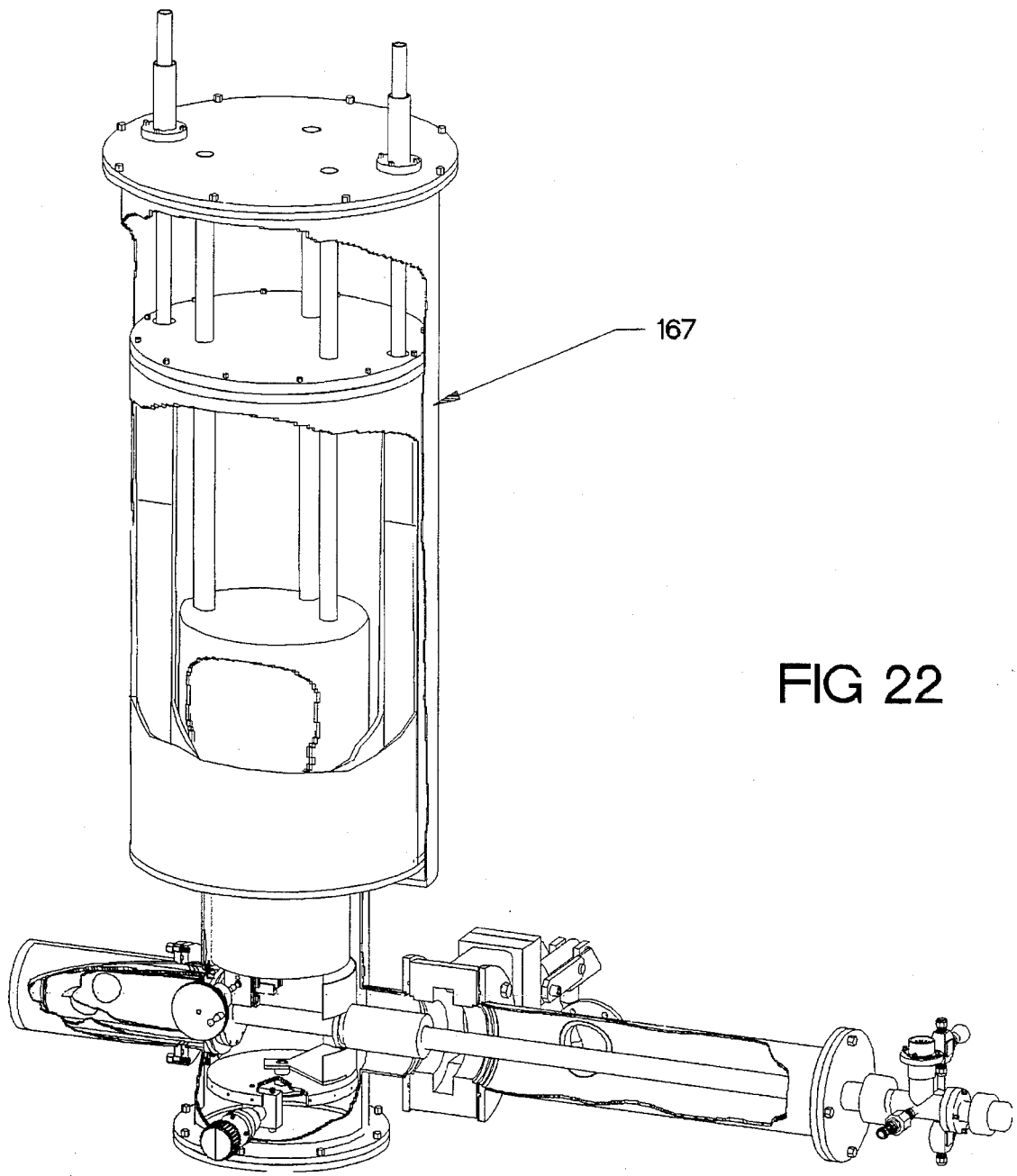
FIG. 22 shows the interface mounted on a liquid helium dewar.

Finally FIG. 22 gives an illustration of how a cooling source other than the mechanical expander 21 is operated in a closed Gifford- McMahon cycle may be used. FIG. 22 shows a cold stage cooled by a liquid helium bath at 4.2 K and a second stage cooled by a liquid nitrogen bath at 77 K. The lower vacuum chamber 30, the radiation shield 22 with its rotating shutter are all transported with no modification to the liquid helium dewar 167. The heat switch 27 is thermally secured to the bottom piece of the liquid helium bath. The measure of flexibility of the system can be demonstrated from the fact that all the independent measurement insert 41 configurations can be loaded according to the standard loading sequence given above. A completely configured and operative experiment can be unloaded from a cryocooler cooled interface and then loaded into the liquid helium dewar with no modification. With the high cryogenic efficiency of the perpendicular loading system helium loss rates can be kept under one liter liquid per day even with very large diameter experiments.

Although the description above contains many specificities, theseshould not be construed as limiting the scope of the invention but as merely providing illustrations of some of the presently preferred embodiments of this invention.

Thus the scope of the invention should be determined by the appended claims and their legal equivalents, rather than by the examples given.

I claim:

1. A system for non intrusively loading or unloading an independent measurement insert into or out of the vacuum of a cryogenic interface in a direction perpendicular to the thermal gradient of a cryogenic cooling source, the system being provided with:

(a) an independent measurement insert, (b) a cryogenic cooling source, (c) heat stations thermally secured to cooling stages of the said cryogenic cooling source where the coldest stage of said cryogenic cooling source is designated as the cold stage, (d) a vacuum chamber enclosing a common vacuum space which serves to thermally insulate said heat stations, (e) a heat switch anchored to said cold stage heat station of said cryogenic cooling source for establishing a variable thermal contact between said independent measurement insert and the said cold stage heat station, (f) an enveloping radiation shield thermally anchored to one of said heat stations at a temperature intermediate to the temperature of said cold stage and ambient temperature said enveloping radiation shield posessing an opening which enables access of said perpendicularly loaded independent measurement insert to said heat switch, (g a rotating shutter which rotates about the cylindrical axis of said radiation shield which when in closed position acts so as to thermally shield said cold stage of said cooling source from radiation sourced at temperatures higher than the temperature of said cold stage and and which also enables a thermal contact means between said radiation shield and said insert for the purpose of precooling said insert and when said shutter is partially open and said insert is in loaded position, said shutter engages intermediate stage thermal anchor of said insert so as to locate absorb heat from and support said insert in such a manner that the thermal contact established by means of said heat switch with said base flange may be finely tuned, (h) an air lock chamber which may be partioned from the main vacuum space by means of a vacuum valve and which enables the perpendicula loading of said independent measurement insert into said common vacuum space without degradation of the insulating vacuum.

2. A system for non intrusively loading or unloading an independent measurement insert into or out of the vacuum of a cryogenic interface in a direction perpendicular to the thermal gradient of a cryogenic cooling source according to claim 1, the cryogenic cooling source being selected from a plurality of appropriate cryogenic cooling sources and where said cryogenic interface may be oriented so as to enable either:

(a) top loading of said independent measurement insert along a vertical axis, (b) side loading of said independent measurement insert along a horizontal axis, (c) loading of said independent measurement insert along an axis inclined at an arbitrary angle to said vertical axis.

3. A system according to claim 1, the cryogenic cooling source being comprised of a mechanical expander operating in a closed Gifford McMahon cycle powered by an external helium compressor and where said cryogenic interface may be oriented so as to enable either:

(a) top loading of said independent measurement insert along a vertical axis, (b) side loading of said independent measurement insert along a horizontal axis, (c) loading of said independent measurement insert along an axis inclined at an arbitrary angle to said vertical axis.

4. A system according to claim 1, the cryogenic cooling source being comprised of a liquid helium dewar where said liquid helium dewar and said cryogenic interface are configured and oriented so as to enable either:

(a) top loading of said independent measurement insert along a vertical axis, (b) side loading of said independent measurement insert along a horizontal axis, (c) loading of said independent measurement insert along an axis inclined at an arbitrary angle to said vertical axis.

5. A system according to claim 1 provided with said independent measurement insert comprised of:

(a) a thin wall stainless support tube fitted at the cold end with a copper base flange on which a plurality of fastening means are arrayed for the purpose of mounting and thermally grounding various expermental attachments, heaters and insulating electrical standoffs and fitted on the warm end with a hermetic multiwire feedthrough, (b) a thermal anchor means secured to the back of said copper base flange in such fashion that when engaged with said mechanical heat switch, good thermal contact with said cold stage of said cryogenic cold source is established rsulting in a heat flow from the base flange to the cold stage, (c) a flange provided with a sliding seal through which said stainless support tube slides during loading and unloading procedures, (d) an intermediate stage thermal anchor means thermally secured to the support tube of said independent measurement insert between said copper base flange and said sliding seal, said thermal anchor engaging the rotating shutter prior to the engagement of the heat switch so as to provide thermal anchoring of said support tube of said independent measurement insert at a temperature above that of the cold stage but less than ambient temperature thereby reducing thermal loading of said independent measurement insert upon said cold stage, said thermal anchor and said rotating shutter also locating and fixing said independent measurement insert in correct position for engagement of said heat switch thereby enabling fine tuning of the thermal contact between said independent measurement insert and the heat station anchored to the cold stage of said cryogenic cooling source.

6. A system according to claim 5 provided with:

(a) said independent measurement insert and said copper base flange, (b) exchange gas jacket secured with an indium metal vacuum seal to said copper base flange, said jacket when filled with exchange gas causing a thermal link to be established between said cold stage and an object enclosed within said exchange gas jacket, (c) thermally insulated support for said object within said jacket such that without exchange gas in exchange gas jacket said object is thermally isolated, this arrangement supporting heat flow out of and cooling of said object only when the exchange gas jacket contains exchange gas, this arrangement enabling cryogenic measurements requiring electrical isolation of a sample such as in magnetic ac susceptibility measurements or in measurements requiring vibration isolation.

7. A system according to claim 5 provided with a solid heat conductive thermal link and sample holder thermally secured to said copper base flange, this being an arrangement suitable, for instance, for four wire resistivity measurements on superconductors where it is desirable that samples be loaded directly into vacuum and and also being an arrangement suitable for other measurements where thermal contact with said cold stage is to be established via a solid conductive heat link.

8. A system according to claim 5 where in addition quick loading and unloading of an object to be cooled without loading or unloading of independent measurement insert is enabled by the following provisions:

(a) said object to be supported on a tube of low thermal conductance, (b) said support tube being supported at warm end of independent measurement insert by said sliding seal secured to a demountable flange, (c) said demountable flange enabling insertion of or removal of object and support tube from interion of independent measurement insert support tube, (d) said sliding seal enabling insertion and removal of object and support tube from interion of exchange gas jacket without loss of exchange gas, (e) thermal contact between object to be cooled and said insert flange base plate to be mediated by insertion of exchange gas into said exchange gas jacket.

9. A system according to claim 1 where the loading method is comprised of the following sequence of steps:

(a) with said vacuum valve and said rotating shutter closed bolt said independent measurement insert onto airlock chamber ring flange and pump down said airlock to a thermally insulating vacuum, (b) open said vacuum valve and said rotating shutter, advance independent measurement insert through sliding seal and engage precooling thermal anchor in notch of said rotating shutter by partially closing said rotating shutter, (c) when the heat content of the cold end of said independent measurement insert falls below a level which can readily absorbed by the cryogenic cooling source with only a short term disruption of the cryogenic cooling source operating point, reopen said rotating shutter further advance independent measurement insert through sliding compression seal and then engage intermediate stage thermal anchor with said rotating shutter, (d) engage heat switch with back flange thermal anchor of said independent measurement insert and adjust thermal impedance between said independent measurement insert and cold stage to value appropriate to the operating temperature of said independent measurement insert.

10. A system to claim 1 where the unloading method is comprised of the following sequence of steps:
  (a) disengage said heat switch from said base flange thermal anchor of said independent measurement insert,
  (b) reopen said rotating shutter and withdraw said independent measurement insert through sliding seal until cold end of said independent measurement insert is entirely within said airlock chamber,
  (c) close said rotating shutter to shield said cold stage from thermal radiation sourced at ambient temperature,
  (d) close said vacuum vane and vent said airlock with fast opening and closing of airlock pumping valve to ambient air pressure so as to admit a fraction of an atmoaphere of air into said airlock containing insufficient moisture for condensing water on cold end of said independent measurement insert,
  (e) unbolt said independent measurement insert from said airlock chamber ring flange.

* * * * *